(12) United States Patent
Djordjevic (10) Patent No.: US 8,100,581 B2
(45) Date of Patent: Jan. 24, 2012

(54) METHOD OF DETERMINING THE PRESENCE OF A MINERAL WITHIN A MATERIAL

(75) Inventor: Nenad Djordjevic, Brookfield (AU)

(73) Assignee: The University of Queensland, Queensland (AU)

( * ) Notice: Subject to any disclaimer, the term of this patent is extended or adjusted under 35 U.S.C. 154(b) by 618 days.

(21) Appl. No.: 12/084,492

(22) PCT Filed: Oct. 23, 2006

(86) PCT No.: PCT/AU2006/001561
§ 371 (c)(1),
(2), (4) Date: Mar. 16, 2009

(87) PCT Pub. No.: WO2007/051225
PCT Pub. Date: May 10, 2007

(65) Prior Publication Data
US 2009/0314086 A1    Dec. 24, 2009

(30) Foreign Application Priority Data

Nov. 4, 2005 (AU) .............................. 2005-906115

(51) Int. Cl.
*G01J 5/00* (2006.01)

(52) U.S. Cl. ................................. 374/122; 374/4; 374/45
(58) Field of Classification Search .................. 374/4, 5, 374/120, 122, 45.7, 45, 47
See application file for complete search history.

(56) References Cited

U.S. PATENT DOCUMENTS

| 5,170,666 A | 12/1992 | Larsen |
| 5,209,355 A * | 5/1993 | Mindermann ................. 209/3.1 |
| 2009/0245320 A1 * | 10/2009 | Timans ............................. 374/2 |

FOREIGN PATENT DOCUMENTS

| GB | 2188727 | 10/1987 |
| GB | 2206213 | 12/1988 |

* cited by examiner

*Primary Examiner* — G. Bradley Bennett
(74) *Attorney, Agent, or Firm* — Peter F. Corless; Christine C. O'Day; Edwards Wildman Palmer LLP (57) ABSTRACT

The invention relates generally to a method of determining the presence of a mineral within a material, such as a rock, a rock fragment, soil, sand or other geological material including: applying pulsed microwave radiation to the material; detecting radiation emitted from the material after the application of the pulsed microwave radiation; and analysing the detected radiation to determine the presence of mineral within the material. The invention also provides a method of sorting rock fragments into at least two streams using this method and an apparatus for carrying out the method.

29 Claims, 6 Drawing Sheets

METHOD OF DETERMINING THE PRESENCE OF A MINERAL WITHIN A MATERIAL

FIELD OF THE INVENTION

The invention relates primarily to a method of determining the presence or absence of a mineral within a material, be that a rock fragment in the laboratory or a rock body in situ, for example. The invention also relates to a method of sorting rock fragments, such as ore fragments, based on a determination according to the above method. Still further, the invention relates to an apparatus for determining the presence of a mineral within a material.

The invention has particular but not exclusive application to assessing mineral content and/or distribution within and on the surface of rock fragments, and for illustrative purposes particular reference will be made to this application. However, it is to be understood that this invention could be used in other applications, such as assessing mineral content and or distribution within rock bodies in situ, in soils or sands, in mining, in other geological contexts and in research.

BACKGROUND TO THE INVENTION

It has been known for a relatively long time that dielectric (non-metallic) materials can be heated by applying energy in the form of microwaves. The origin of such heating is derived from the ability of the electric field to polarise charges in the material and the inability of this polarisation to follow rapid reversals of the external electromagnetic field. The ability of a material to be heated by microwaves depends on its complex permittivity and loss tangent. Complex permittivity is described by equation (1):

$$\in^* = \in' - j\in''\text{eff} \quad (1)$$

where real part ($\in'$) is a measure of how much energy from the external field is stored in the material; and the imaginary part ($\in''\text{eff}$) is the effective loss factor and is a measure of how dissipative the material is to an external field.

Loss tangent is defined by equation (2) and represents a ratio of energy lost and energy stored, per cycle of field oscillation.

$$\tan \delta\text{eff} = \in''\text{eff}/\in' \quad (2)$$

Both parameters are a function of frequency and temperature.

Rate of temperature rise within material exposed to microwave radiation is given by equation (3):

$$DT/dt = \text{const.}^* \in''\text{eff}^* f^* E^{\wedge}2/\rho^* Cp \quad (3)$$

where E is intensity of electromagnetic field; $\in'''\text{eff}$ is loss factor; f is microwave frequency; $\rho$ is material density; and Cp is specific heat capacity of the material. Hence for a given material and microwave cavity, the rate of material heating will increase with an increase in the frequency of the microwaves and intensity of electromagnetic field squared.

Optimum transfer of microwave energy can be achieved by ensuring adequate penetration into the material and a high conversion of the microwave energy into heat. This can be achieved if the material has a moderate value of $\in'$ and if the loss factor is high (i.e. a relatively high value of $\in''\text{eff}$ resulting in a relatively high value of $\tan \delta\text{eff}$). Water is characterised by a strong ability to absorb microwave energy and transform that energy into heat.

Rocks typically comprise an aggregate of minerals in varying concentrations and at least some water, either absorbed or chemically bound. Early methods of analysing fragmentary rock samples have included irradiating the samples with microwave radiation for relatively long periods of time, generally in the order of several seconds or more. The microwave radiation differentially heats the rock fragments as observed by, for example, thermal imaging such as by an infra-red camera. Different fragments and/or areas of fragments of the rock sample are composed of different minerals and/or have different water contents. As such, these areas will increase in temperature at a different rate, and therefore to a different degree, in response to the microwave radiation. However, when constant microwave radiation is used rock fragments tend to heat very quickly throughout, reducing the detectable difference between the different components within the rock sample and forming the surface of the rock sample. The resulting infra-red thermal image tends to be essentially a blurry and indistinct depiction of the entire fragment.

In this way fragments containing some minerals which will heat and provide a generally blurry infra-red image can be sorted from those containing very little or no minerals which will heat only mildly to provide a very faint infra-red image. However, the efficacy of the sorting method is not high as it does not allow for the assessment of the level of microwave heating-associated mineral within the rock. Rather it provides a rudimentary analysis of whether the fragment contains desired minerals or not. Furthermore such methods do not provide any information about the pattern of mineral distribution in the rock fragments. For example such methods could not provide an assessment of whether the mineral deposits are located in the centre or on the surface of the rock. Due to their relative insensitivities, prior art methods have been primarily focused on separating rocks based on the different amounts of absorbed water within the rocks.

Pulsed microwave radiation has been used for inducement of micro-fractures in rock fragments to reduce the amount of energy required for subsequent crushing and comminution. The power density absorption of the microwave radiation used for this practice is generally in the range of 1,000 to 100,000 MW/m$^3$. However, these processes with such high microwave power densities are not suitable or required for the analysis of mineral content within or on the surface of rock fragments.

Thus, it would be advantageous if a method could be provided for determining the presence of mineral within a rock more distinctly and thereby effectively enable sorting of rock fragments containing different amounts of minerals. It would also be advantageous if a method were provided that facilitates determination of the pattern of valuable mineral distribution within or on the surface of the rock fragments.

It has been surprisingly found that pulsed microwave irradiation at lower power densities than those used for the inducement of micro-fractures in rocks is superior to continuous wave microwave irradiation for analysis of the content of microwave-absorbing minerals in fragmentary samples. The use of such irradiation may allow not only the identification of fragments containing minerals but also quantification of the mineral content.

SUMMARY OF THE INVENTION

In one aspect of the present invention there is provided a method of determining the presence of a mineral within a material including:
applying pulsed microwave radiation to the material;
detecting radiation emitted from the material after the application of the pulsed microwave radiation; and analysing the detected radiation to determine the presence of the mineral in the material.

As used herein the term "mineral" is intended in a broad sense. This term includes within its scope both non-organic minerals, such as chalcocite, chalcopyrite, galena, magnetite, hematite, pyrite, pyrhotite, sphaleraite, uraninite, etc., and organic geological compounds, such as heavy oil, light oil, bitumen, etc.

As used herein the term "material" is intended in a broad sense. This term includes within its scope rocks, rock fragments, soils, sands and other geological materials whether in situ or not.

The microwave pulse duration is advantageously chosen such that:
- the heating of surface moisture and/or absorbed moisture within the material is minimised;
- the thermal differential between the microwave absorbing minerals and other material is maximised;
- the heating of gangue material is minimised; and/or
- the mineral of choice in the material is suitably affected by the microwave pulse.

In certain embodiments the pulsed microwave radiation applied to the material includes at least one pulse of up to 1 second duration, preferably from 0.01 to 1 second duration and more preferably from 0.1 to 1 second duration. In other embodiments the pulsed microwave radiation applied to the material includes a plurality of pulses of up to 1 second duration, preferably from 0.01 to 1 second duration and more preferably from 0.1 to 1 second duration.

As described briefly above, where the material includes rocks or rock fragments, the pulsed microwave radiation is generally applied at relatively low power densities so as to avoid any inducement of micro-fractures in the rock fragments. This amount of microwave irradiation that will induce fracture will vary from case to case as will be appreciated by those of skill in the art. In a preferred embodiment the pulsed microwave radiation is applied at a power density below 1,000 MW/m$^3$, more preferably in a range of from 1 to 100 MW/m$^3$.

In a similar vein to selection of the microwave pulse duration, the microwave frequency may be chosen to:
- minimise the heating of the surface moisture and/or the absorbed moisture within the material;
- maximise the thermal differential between the microwave absorbing minerals and the other material;
- suit a mineral of choice; and/or
- minimise the heating of gangue material.

The frequency will preferably be in the range of from 900 to 5800 MHz, more preferably in the range of from 900 to 3500 MHz, even more preferably from 915 to 2450 MHz, and most preferably in the range of from 915 to 950 MHz.

The method of detection of radiation emitted from the material is not particularly limited. In one embodiment, the detection of radiation emitted from the material includes thermal imaging of the material, for example using an infra red camera. In another embodiment the detection of radiation emitted from the material includes detecting microwave radiation emitted from the material, for example using passive microwave sensing.

Generally, the mineral being targeted in each particular case will be known. As such, the infra red spectra of the mineral being targeted will also generally be known, or can be determined. Where thermal imaging is the analysis method of choice, it is preferred that infrared imaging be performed within the spectral range of infra red radiation within which the targeted mineral is characterised as having its highest differential emmisivity relative to the host (background) rock or soil.

As mentioned above, the method of the invention may be applicable for in situ analysis of the material, for example for determining mineral content in a body or ore in situ. Generally, the method is applicable to rock fragments or other material samples, such as sand samples or soil samples that are removed from their in situ site. In that case, the material is preferably fed into a microwave irradiation zone for subsequent application of the pulsed microwave radiation.

The material may be fed into the microwave irradiation zone in a single feed channel. Alternatively, to increase throughput the material may be fed into the microwave irradiation zone in a plurality of separate feed channels. In either case, where the material includes rocks or rock fragments, the rocks or rock fragments are preferably fed into the microwave irradiation zone single file in the one or more channels.

In certain embodiments it may be desirable to apply more than one microwave frequency to the material being analysed. This may provide a more detailed analysis of the make-up of the material sample as described below.

Accordingly, in another aspect the invention provides a method of determining the presence of a mineral in a material including:
- applying pulsed microwave radiation of a first frequency to the material;
- detecting a first amount of radiation emitted from the material after the application of the pulsed microwave radiation of the first frequency;
- applying pulsed microwave radiation of a second frequency to the material;
- detecting a second amount of radiation emitted from the material after the application of the pulsed microwave radiation of the second frequency; and
- analysing the detected first and second amounts of radiation to determine the presence of the mineral within the material.

Efficiency of penetration of microwave energy into a material, described as the depth at which the intensity of the microwave field decays by a factor of (1/e) or approximately 37% of initial intensity, is described by a parameter (skin depth) which is a function of the dielectric properties of the material as well as the frequency of microwave radiation applied. This is defined by equation (4):

$$\delta = (c/f)((\in')^{\wedge}0.5/(2\pi \in"\text{eff})) \qquad (4)$$

where ($\delta$) is skin depth; (c) is propagation velocity of electromagnetic waves through the material; (f) is the frequency of microwaves applied; and $\in'$ and $\in"$eff are real and imaginary parts of the complex dielectric permittivity of the material.

All of these parameters, except microwave frequency, are constant for a given material. So, for a given host rock, (i.e., constant dielectric parameters) frequency of the microwave source will determine effective depth of microwave heating.

In the case of a material having relatively deeply embedded microwave absorbing minerals, by using two microwave frequencies it is possible to distinguish between microwave absorbing minerals at or close to the surface from the strongly microwave absorbing minerals located at depth within the material.

Heating of the microwave absorbing minerals inside the material, for example a rock or rock fragment, is not immediately evident on the surface of the material in terms of thermal pattern produced. Due to the relatively low thermal conductivity of such materials, it may take up to several seconds for heat to reach the surface of the material. This is particularly the case when the material is a rock or rock fragment.

In the first stage of this aspect of the invention, microwave radiation is applied at a first frequency which is generally a relatively high frequency microwave radiation, for example from 920 to 925 MHz. Of course other frequencies may be employed within the preferred ranges mentioned above. If the material contains microwave absorbing minerals on its surface, this will be immediately recognised by the following analysis, which may be conducted using the methods previously described. Such fragments will be immediately removed for further processing.

In the second stage of this aspect of the invention, microwave irradiation is applied at a second frequency which is generally a relatively low frequency microwave radiation, for example from 915 to 920 MHz. Again, other frequencies may be applied as mentioned above. This will allow for more efficient deep penetration of microwaves into the material and heating of microwave absorbing minerals within the material. Due to the time required for this heat to reach the surface of the material, the material will preferably be analysed some time after application of the microwave radiation. For example, the material may be analysed from 1 to 5 seconds after microwave application. This may again be achieved using the analysis methods described above.

It will be appreciated that the first frequency may be a high frequency and the second frequency a low frequency if desired in a particular application.

By exposing materials, particularly rocks or rock fragments, to a relatively high frequency microwave radiation, analysing the resulting radiation (for example the thermal pattern) emitted from the material, and subsequently exposing the material to a relatively high frequency microwave radiation, preferably at the same energy, and again analysing the resulting radiation emitted from the material, the difference between those two emissions will reveal the existence of microwave absorbing minerals which are located deep in the interior of the material.

Where images are produced following from the application of the first and second microwave frequencies, image processing techniques, such as the subtraction of the $1^{st}$ image from the $2^{nd}$ image may enhance features indicating existence of hot, relatively deeply buried, microwave absorbing minerals. Materials exhibiting such a thermal anomaly will be extracted for further processing.

Hence, by using two different microwave frequencies it is possible to distinguish between materials, particularly rock and rock fragments, containing microwave absorbing minerals on the surface, from those where microwave absorbing minerals are not visible on the surface, but are embedded within the material.

Further to the above, from the rate of temperature decay normalised with the mass and size of the material sample being analysed, it may be possible to determine the mass of the microwave absorbing minerals of certain kind that are present within the material. This will provide advantages as would be appreciated by those of skill in the art.

It should be appreciated that additional steps may be included. For example, the method may include at least one further application of microwave radiation of a frequency different to the first and second frequencies to the material, and subsequent detection of the amount of radiation emitted from the material According to another aspect of the invention there is provided a method of sorting a feed stream of material into at least two streams including:

determining the presence of a mineral in the feed stream of material using a method as described above; and separating the feed stream of material into the at least two streams based on that determination.

According to this aspect of the invention, the feed stream is preferably separated into at least a waste stream and a product stream. In certain embodiments, the feed stream may be separated into a waste stream and a plurality of product streams based on mineral grade of the material.

Separation of the feed stream into at least two separate streams may be achieved by any suitable means. For example this may be achieved using a separating conveyor belt or the like. Preferably, the feed stream is separated into the at least two streams by a high pressure air blower.

According to yet another aspect of the invention there is provided an apparatus for determining the presence of a mineral within a material including:

a microwave irradiation zone including a microwave emitter adapted to emit pulsed microwave radiation into the microwave irradiation zone;

a detector for detecting radiation emitted from the material following application of pulsed microwave radiation to the material; and an analyser for interpreting the radiation detected and thereby determining the presence of the mineral within the material.

Preferably the microwave irradiation zone, including the microwave emitter, is arranged such that the material being analysed passes vertically through the microwave irradiation zone. In that way, the material being analysed may simply fall under gravity through the microwave irradiation zone.

In order to facilitate the processing of a large volume of material in a uniform and continuous manner, the microwave emitter will most likely be in the form of a multimode microwave cavity, preferably equipped with a suitable stirrer. Advantageously, use of such a microwave cavity will ensure that all microwave resonance modes within cavity are excited ensuring as uniform heating of the material as possible. Use of a suitable single mode microwave cavity could provide more efficient heating of the material from an energy consumption point of a view.

As will be appreciated from the above description of the invention generally, the detector is preferably a thermal imager or a passive microwave sensor.

If a thermal imager is employed, this may be an infra-red imager. Furthermore, the apparatus may include additional thermal imagers. In one embodiment, the apparatus further include a cool region, the cool region being of relatively lower temperature to the rest of the apparatus. The thermal imager/s may then be positioned about the cool region providing for improved detection of radiation emitted from the material as it passes through the microwave irradiation zone.

Considering that the speed of the material through the microwave irradiation zone could be up to several metres per second, it is important that the material residence time within microwave irradiation zone is sufficiently long to induce the required amount of heating of the minerals of interest to allow for their efficient identification. Preferably, the microwave absorbing minerals will be heated to a temperature which is significantly higher (10-50° C.) from the temperature of the microwave non-absorbing minerals. Considering that thermal sensitivity of modern IR imaging systems is about 0.02° C., microwave absorbing minerals and their pattern of distribution within the material will be easily recognised by thermal imaging.

As noted, the detector may include a passive microwave sensor, or a plurality of such sensors. In that case, after passing through the microwave irradiation zone, the presence of microwave absorbing minerals will be detected by using the passive microwave sensor (i.e. a radiometer). Such sensors are in effect microwave receivers of high precision and are able to detect electromagnetic radiation coming from the material in the microwave part of the electromagnetic spectrum. This allows for the detection heated minerals which have absorbed microwave radiation while passing through the cavity, not only on the material surface, but also embedded relatively deeply in the material. This is due to fact that microwaves have a greater wavelength compared to the infrared radiation.

In this embodiment, detection of microwave absorbing minerals is not based on detection of microwave radiation that this transmitted through the investigated material, but is based on the detection of natural microwave electromagnetic radiation coming from the previously heated material. In that regard, passive microwave sensors are similar in concept to infrared sensors. According to Plank's radiation law all objects emit microwave energy of some magnitude, but the amounts are generally very small. The amount of energy emitted from the material is proportional to the temperature of the material. A passive microwave sensor detects the naturally emitted microwave energy within its field of view. Microwave radiation is generally detected using an antenna of a suitable type (most likely a horn antenna).

Because of their longer wavelengths, compared with infrared radiation, microwaves have properties that are advantageous for the detection of valuable minerals. Longer wavelength microwave radiation can penetrate through dust as the longer wavelengths are not susceptible to atmospheric scattering which affects shorter optical wavelengths (infrared and visible). This property allows for the detection of microwave energy under almost all environmental conditions so that data can be collected at any time.

The analyser will generally be a computer equipped with image processing software. Advantageously, this will enable continuous and automated processing and analysis of a feed of material.

In certain embodiments, it may be desirable for the apparatus to include a visible light camera or other means for gauging the size of material passing through the microwave irradiation zone. This may particularly be the case where the material includes rocks or rock fragments.

The apparatus of the invention will preferably be configured to facilitate sorting of material passing through the microwave irradiation zone. Preferably, therefore, the apparatus includes a sorter for sorting the material into at least two streams. The sorter may include a separating conveyor belt, but is preferably a high pressure air blower. A plurality of high pressure air blowers may be included if desired.

The material may be fed to the microwave irradiation zone by any suitable means. However, the apparatus preferably includes a feeder for supplying the material to the microwave irradiation zone in at least one channel. Preferably the feeder is a conveyer belt.

In certain embodiments, the continuous monitoring of moisture within material may be a useful addition that will improve efficiency of sorting process. As such, a monitor may be provided to facilitate this.

DETAILED DESCRIPTION OF THE INVENTION

It will be convenient to hereinafter provide a detailed description of certain embodiments of the invention with reference to the accompanying drawings. The purpose of providing this detailed description is to instruct persons having an interest in the subject matter of the invention how to put the invention into practice. It is to be clearly understood however that the specific nature of this detailed description does not supersede the generality of the preceding statements.

Figure 1:
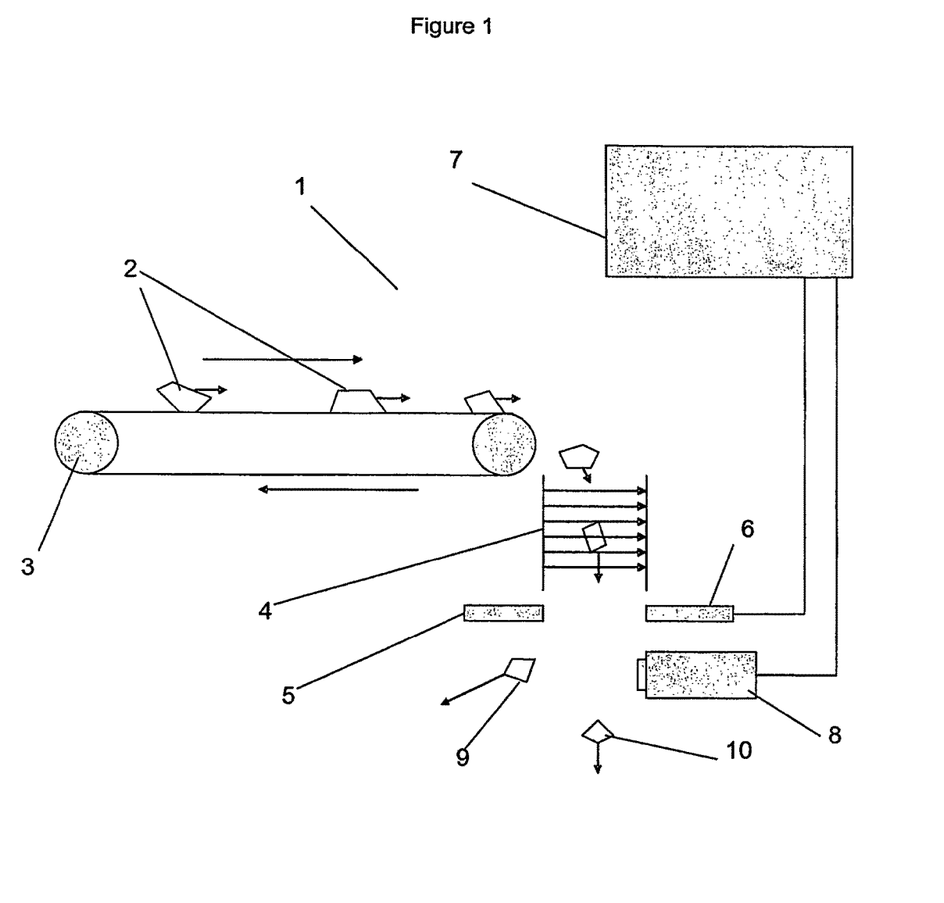
FIG. 1 illustrates an apparatus according to one embodiment of the invention.

FIG. 1 depicts an apparatus (1) in accordance with one embodiment of the present invention. Rock fragments (2) are transported by a conveyor belt (3) that terminates above a microwave irradiation zone in the form of a multimode or single mode microwave cavity (4). The rock fragments (2) fall vertically through the microwave cavity (4). Although the rock fragments (2) may pass through the cavity (4) in any direction, falling vertically is advantageous as it increases the likelihood of even distribution of the irradiation of the fragments as they tumble through the cavity (4). The rock fragments pass through the cavity (4) individually so that each fragment (2) may be analyzed individually.

Within the microwave cavity (4) the rock fragments (2) are exposed to short pulsed microwave radiation of a selected frequency and intensity. As previously noted, the microwave radiation will generally have a frequency from 900 to 5800 MHz, although the frequency will obviously be quite variable depending on the mineral or grade of interest. Generally, a frequency in the lower end of this range will be employed. The pulsed microwave radiation may be applied at a power density below that which is required to induce micro-fractures in the rock fragments as previously described. Generally, the pulsed microwave radiation will be applied at a power density of below 1000 MW/m$^3$.

Immediately after passing through the microwave cavity (4), radiation emitted from the rock fragments (2) is detected by high resolution, high speed infrared imager (5) and (6). As previously noted, other forms of detection may be used according to the invention. In this embodiment the imagers (5,6) capture thermal images of the rock fragments (2). While one thermal imager is sufficient, two or more thermal imagers (5,6) may be used for full coverage of the rock particle surface. Images collected by the thermal imagers (5,6) are processed using a computer (7) equipped with image processing software. The thermal imagers (5,6) may also be used for determination of the size of the rock fragments (2).

Alternatively, or in combination, one or more visible light cameras may capture visible light images to allow determination of fragment size. From the number of detected hot spots (pixels), temperature, pattern of their distribution and their cumulative area, relative to the size of the fragment, an estimation of the grade of observed rock fragments will be made. This estimation may be supported and/or more mineral content may be quantified by comparison of the data with previously established relationships between microwave induced thermal properties of specifically graded and sized rock fragments.

Based on the content analysis individual rock fragments (2) may then be separated using a separator in the form of a high pressure air blower (8). Any appropriate conventional device may, however, be used as described above. The air blower (8) separates the individual rock fragments (2) based on information sent by the computer (7). The individual rock fragments (2) may be separated on the basis of, for example, estimated grade, quantified mineral content and/or location of mineral pockets within or on the surface of the rock fragments (2).

In the apparatus depicted in FIG. 1, the high pressure air blower (8) may receive a signal from the computer (7) to release air at the moment a rock fragment containing a high mineral content (9) passes it such that that fragment (9) is directed to a specific collector. Low grade or gangue particles (10) may be allowed to continue their free fall into a separate collector. In this particular embodiment for ease of understanding the fragments have only been divided into two groups. However, it should be realized that this apparatus and method can be configured to separate the rock fragments (2) across a scale of mineral content. In such a configuration, the high pressure air blower (8) may blow air at varying forces and/or directions, or multiple blowers could be used, for example for each fragment grade, to direct specific fragments to specific collectors dependent upon the level of mineral content or distribution pattern of the mineral within the fragments. Alternatively, or in combination, separate conveyer belts may be used to direct the rock fragments to separate collectors.

As discussed above, previous methods employing constant high power microwave irradiation have resulted in heating of rock fragments throughout producing a blurry thermal image. The resultant images have been limited to essentially allowing determination of those rock fragments containing minerals of interest and those not containing the mineral. The use of pulsed lower power microwave irradiation enables the mineral pockets in the rock fragments and/or on the surface of the rock fragments to heat quickly without distributing heat rapidly to the surrounding rock. Accordingly, the resultant thermal image may be far more defined and in many cases the image will allow the mineral pocket to be pinpointed within the rock fragment. One obvious advantage of this is that a more accurate quantification of mineral content is achieved. One follow on advantage is that rock fragments may be sorted across a scale of mineral content rather than a rudimentary analysis of high level or low/no mineral content.

In order to illustrate the invention in further detail, reference is now made to FIGS. 2 through 11. The differential heating of the various rock fragments is clearly illustrated in these figures which will be described briefly below.

Figure 2:
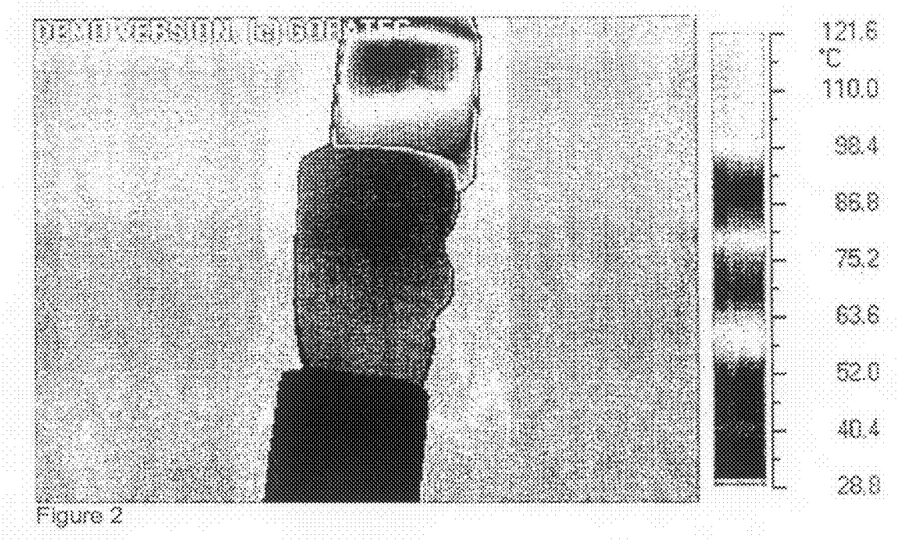
FIG. 2 is an IR image of a high grade copper ore, medium grade copper ore and a barren rock after brief exposure to microwave heating.

FIG. 2 illustrates a high grade copper ore at the top of the Figure. This fragment of ore clearly has higher temperature than the other fragments that have been imaged. The middle fragment of this image is a medium grade copper ore. It will be appreciated on viewing the image that the medium grade ore is much duller and therefore has a lower temperature than the high grade ore after the same amount of microwave irradiation has been applied. Likewise, the barren rock, which is located at the bottom of the image, is black, indicating very little heating of that fragment after the same amount of microwave irradiation.

Figure 3:
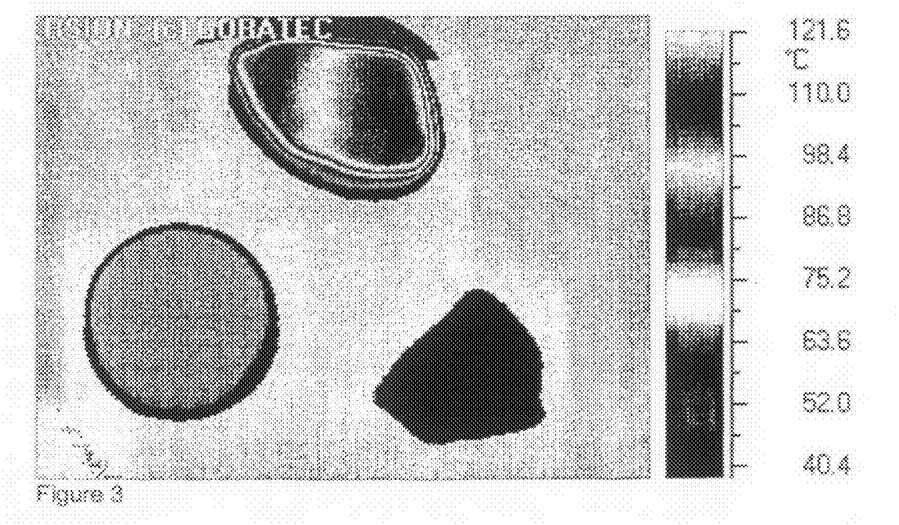
FIG. 3 is an IR image of a high grade ore fragment, a sandstone fragment and waste rock after brief exposure to microwave heating.

FIG. 3 similarly provides an image of a high grade ore fragment at the top, a sandstone fragment at the lower left and a waste rock at the lower right. Once again, the high grade ore sample shows markedly higher temperature than the other two samples.

Figure 4:
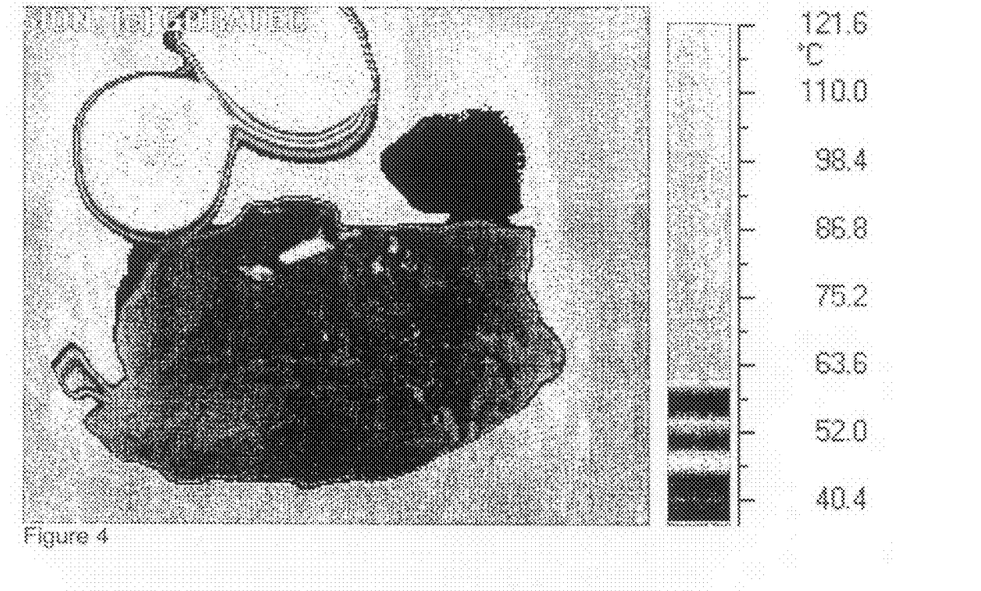
FIG. 4 is an IR image of a high grade copper ore, homogenous sandstone, waste rock and low grade copper ore after brief exposure to microwave heating.

FIG. 4 is an image of simultaneously microwave heated rock fragments, including a high grade copper ore at the top, a homogeneous sandstone fragment at the middle left, a waste rock at the middle right and a low grade copper ore at the bottom. Again, the delineation between the grades of the various fragments is clear in this image.

Figure 5:
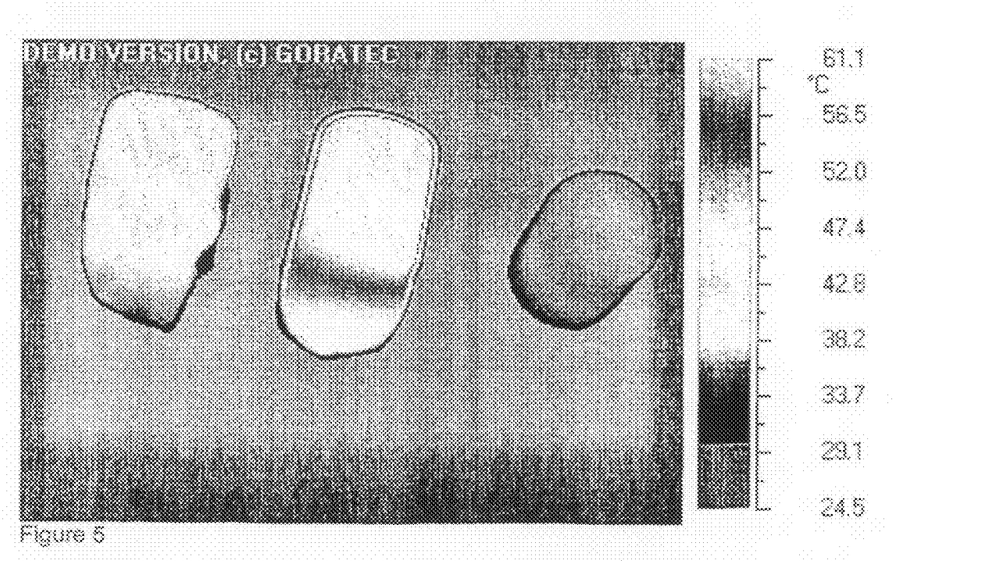
FIG. 5 is an IR image of a mid-grade copper ore, high grade copper ore and granite sample after brief exposure to microwave heating.

FIG. 5 is an image of a high grade copper ore in the middle, which is quite clearly distinct from the lower grade copper ore on the left. The granite sample on the right is easily distinguished from the two copper ore samples.

Figure 6:
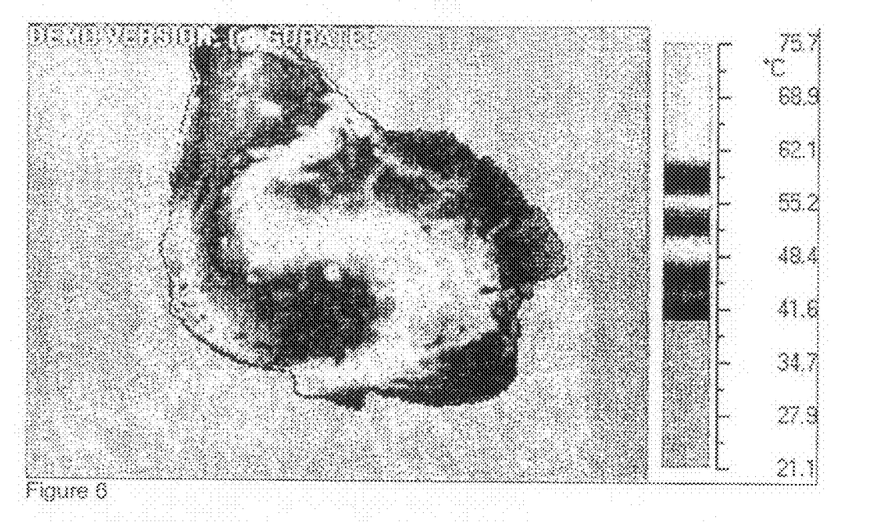
FIG. 6 is an IR image showing increased mineralization corresponding to the warmer part of the rock after brief exposure to microwave heating.

FIG. 6 is an image of a rock fragment that has varying degrees of mineralization throughout its structure. From this image it can be seen how the invention may be used to clarify where mineralization, corresponding to higher temperature after microwave irradiation, is located on the fragment.

Figure 7:
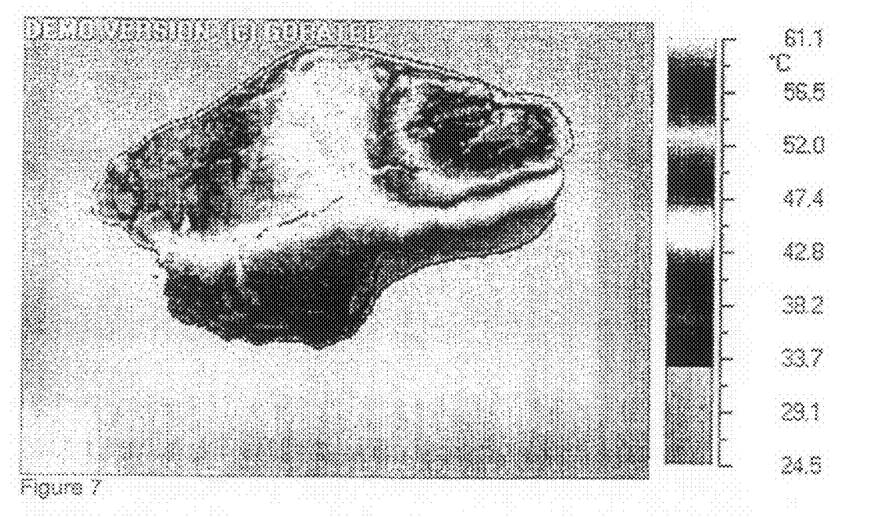
FIG. 7 is an IR image showing not only a highly mineralized part of the rock but also structural features such as cracks, after brief exposure to microwave heating.

FIG. 7 illustrates that brief exposure to microwave radiation may not only provide an indication of the location of mineralization within a rock fragment, but may also provide information on structural features. In this image a crack is clearly visible after the fragment has been briefly exposed to microwave radiation.

Figure 8:
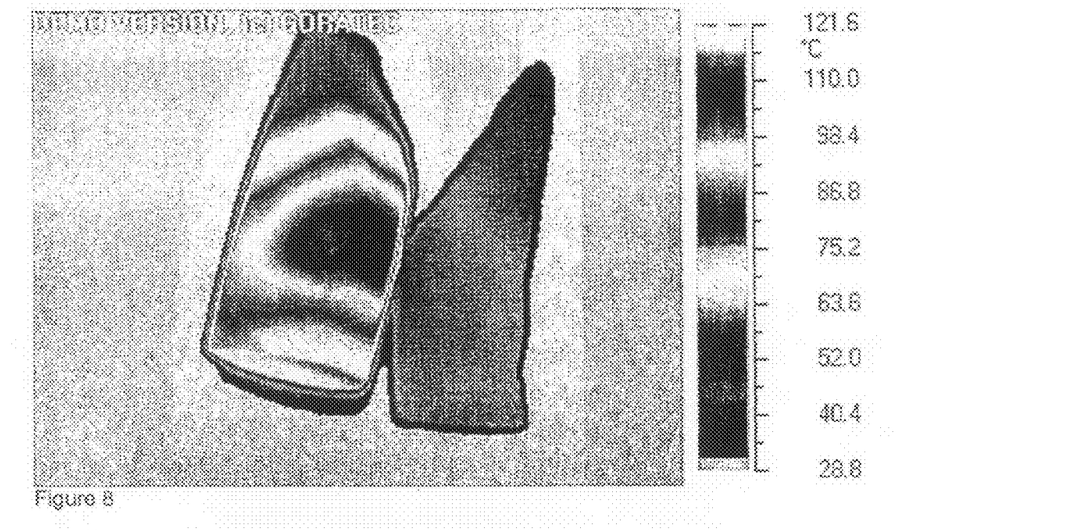
FIG. 8 is an IR image of a copper ore fragment vs. non-mineralised volcanic rock after brief simultaneous exposure to microwave heating.
Figure 9:
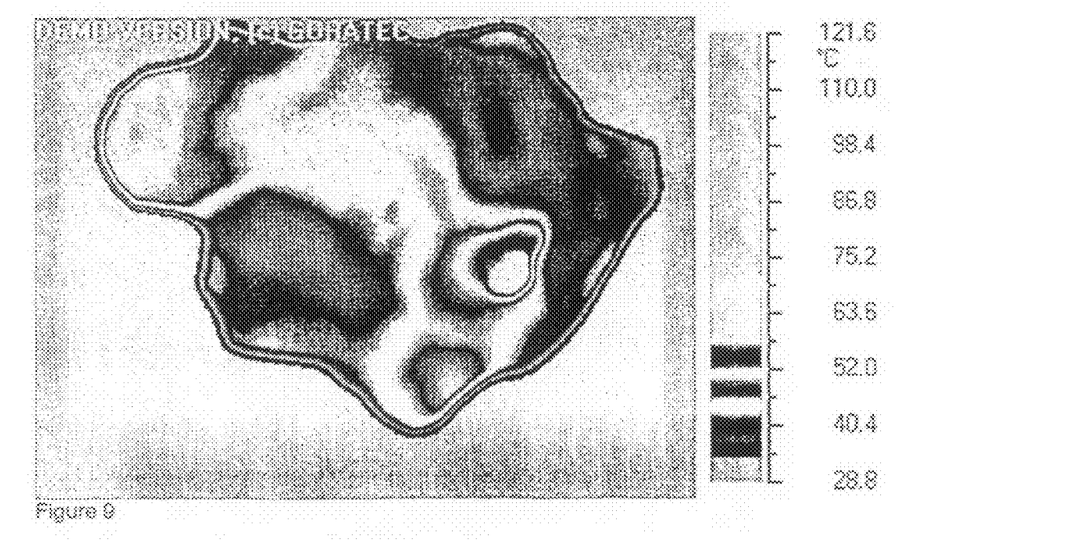
FIG. 9 is an IR image of highly mineralised area within rock is warmer than rest rock surface after brief exposure to microwave heating.

FIG. 8 show the difference between a copper ore fragment on the left and a non-mineralized volcanic rock on the right after simultaneous exposure to microwave radiation.

FIG. 9 again shows differential heating of mineralized areas within a rock fragment after the application on microwave radiation.

Figure 10:
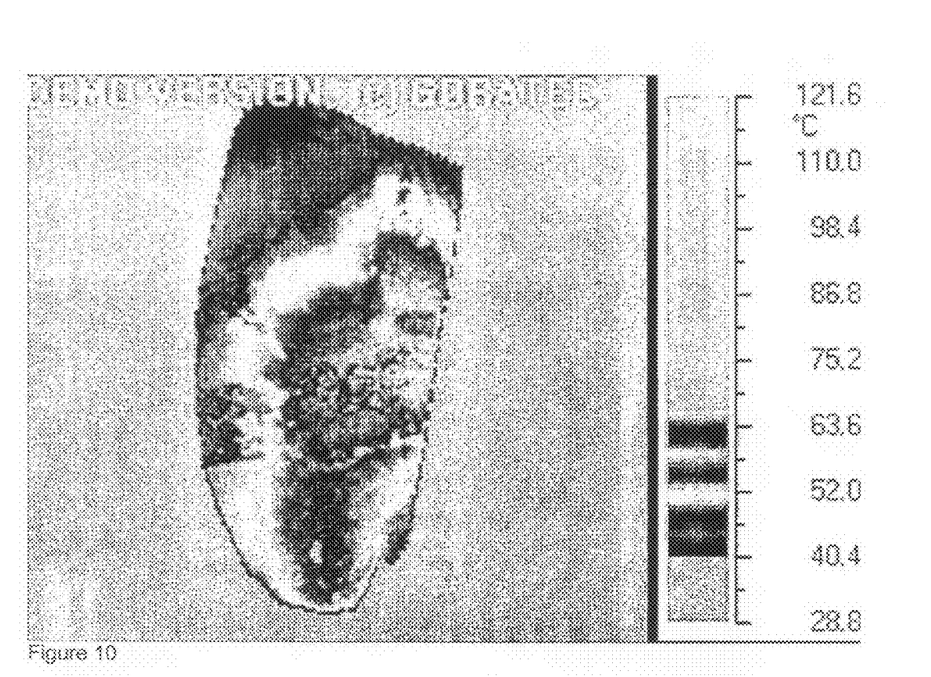
FIG. 10 is an IR image of the mineralised pattern within porphyry copper ore after brief exposure to microwave heating.

FIG. 10 shows the mineralized pattern within a porphyry copper ore sample after exposure to microwave radiation.

Figure 11:
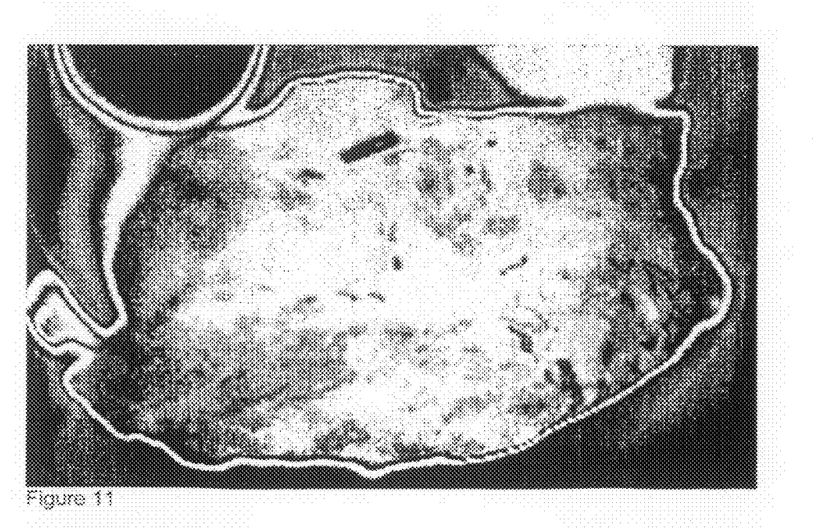
FIG. 11 is an IR image of textural features within an ore fragment after brief exposure to microwave heating.

FIG. 11 shows the textural features within an ore fragment revealed by an infrared image after brief exposure to microwave radiation.

It will of course be realised that the above has been given only by way of illustrative example of the invention and that all such modifications and variations thereto as would be apparent to persons skilled in the art are deemed to fall within the broad scope and ambit of the invention as herein set forth.

The invention claimed is:

1. A method of determining the presence of a mineral in a material including:
   applying pulsed microwave radiation to the material;
   detecting radiation emitted from the material after the application of the pulsed microwave radiation; and
   analysing the detected radiation to determine the presence of the mineral in the material.

2. A method according to claim 1, wherein the pulsed microwave radiation applied to the material includes at least one pulse of up to 1 second duration, preferably from 0.1 to 1 second duration.

3. A method according to claim 1, wherein the pulsed microwave radiation applied to the material includes a plurality of pulses of up to 1 second duration, preferably from 0.1 to 1 second duration.

4. A method according to claim 1, wherein the pulsed microwave radiation has a power density induced within targeted minerals of below 1,000 MW/m$^3$.

5. A method according to claim 4, wherein the pulsed microwave radiation has a power density induced within targeted minerals of from 1 to 100 MW/m$^3$.

6. A method according to claim 1, wherein the pulsed microwave radiation has a frequency of from 900 to 5800 MHz.

7. A method according to claim 6, wherein the pulsed microwave radiation has a frequency of from 900 to 3500 MHz.

8. A method according to claim 7, wherein the pulsed microwave radiation has a frequency of from 915 to 950 MHz.

9. A method according to claim 1, wherein detection of radiation emitted from the material includes thermal imaging of the material.

10. A method according to claim 1, wherein detection of radiation emitted from the material includes detecting microwave radiation emitted from the material.

11. A method according to claim 1, wherein the material is fed into a microwave irradiation zone for subsequent application of the pulsed microwave radiation.

12. A method according to claim 11, wherein the material is fed into the microwave irradiation zone in at least one feed channel.

13. A method of determining the presence of a mineral in a material including:
applying pulsed microwave radiation of a first frequency to the material;
detecting a first amount of radiation emitted from the material after the application of the pulsed microwave radiation of the first frequency;
applying pulsed microwave radiation of a second frequency to the material;
detecting a second amount of radiation emitted from the material after the application of the pulsed microwave radiation of the second frequency; and
analysing the detected first and second amounts of radiation to determine the presence of the mineral within the material.

14. A method according to claim 13, wherein the first frequency is from 920 to 925 and the second frequency is from 915 to 920 MHz.

15. A method according to claim 13, wherein the analysis of the first and second amounts of radiation includes a subtraction of one of the amounts of radiation from the other.

16. A method according to claim 13, including at least one further application of microwave radiation of a frequency different to the first and second frequencies to the material, and subsequent detection of the amount of radiation emitted from the material.

17. A method of sorting a feed stream of material into at least two streams including:
determining the presence of a mineral in the feed stream of material using a method according to claim 1 or claim 13; and
separating the feed stream of material into the at least two streams based on that determination.

18. A method according to claim 17, wherein the feed stream is separated into a waste stream and a product stream.

19. A method according to claim 17, wherein the feed stream is separated into a waste stream and a plurality of product streams based on mineral grade of the material.

20. A method according to claim 17, wherein the feed stream is separated into the at least two streams by a high pressure air blower.

21. An apparatus for determining the presence of a mineral within a material including:
a microwave irradiation zone including a microwave emitter adapted to emit pulsed microwave radiation into microwave irradiation zone;
a detector for detecting radiation emitted from the material following application of pulsed microwave radiation to the material; and
an analyser for interpreting the radiation detected and thereby determining the presence of the mineral within the material.

22. An apparatus according to claim 21, wherein the microwave emitter is a multimode or single mode microwave cavity.

23. An apparatus according to claim 21, wherein the detector is a thermal imager or a passive microwave sensor.

24. An apparatus according to claim 21, wherein the analyser is a computer equipped with image processing software.

25. An apparatus according to claim 21, wherein the material includes rocks or rock fragments and the apparatus includes a visible light camera for gauging the size of the rocks or rock fragments.

26. An apparatus according to claim 21, including a sorter for sorting the material into at least two streams.

27. An apparatus according to claim 26, wherein the sorter is a high pressure air blower.

28. An apparatus according to claim 21, including a feeder for supplying the material to the microwave irradiation zone in at least one channel.

29. An apparatus according to claim 28, wherein the feeder is a conveyer belt.

* * * * *